US011353441B2

(12) United States Patent
Ben Belgacem-Strek

(10) Patent No.: US 11,353,441 B2
(45) Date of Patent: Jun. 7, 2022

(54) METHOD FOR CALCULATING IN REAL TIME THE METHANE NUMBER MN IN THE LIQUID PHASE OF A LIQUEFIED NATURAL GAS

(71) Applicant: ENGIE, Courbevoie (FR)

(72) Inventor: Michel Ben Belgacem-Strek, Paris (FR)

(73) Assignee: Engie, Courbevoie (FR)

( * ) Notice: Subject to any disclaimer, the term of this patent is extended or adjusted under 35 U.S.C. 154(b) by 207 days.

(21) Appl. No.: 16/469,928

(22) PCT Filed: Dec. 15, 2017

(86) PCT No.: PCT/FR2017/053615
§ 371 (c)(1),
(2) Date: Jun. 14, 2019

(87) PCT Pub. No.: WO2018/109418
PCT Pub. Date: Jun. 21, 2018

(65) Prior Publication Data
US 2020/0080984 A1 Mar. 12, 2020

(30) Foreign Application Priority Data
Dec. 15, 2016 (FR) ...................................... 1662507

(51) Int. Cl.
*F17C 13/02* (2006.01)
*G06F 17/11* (2006.01)
*G01N 33/22* (2006.01)

(52) U.S. Cl.
CPC ......... *G01N 33/225* (2013.01); *F17C 13/025* (2013.01); *F17C 13/026* (2013.01); *G06F 17/11* (2013.01); *F17C 2221/033* (2013.01)

(58) Field of Classification Search
CPC ... G01N 33/225; F17C 13/025; F17C 13/026; F17C 2221/033; F17C 13/02; F17C 2250/043; F17C 2250/0447; F17C 2250/0439; G06F 17/11; Y02T 10/30; F02M 21/0215
See application file for complete search history.

(56) References Cited

U.S. PATENT DOCUMENTS

| 5,333,591 A | 8/1994 | Korsmier et al. |
| 6,279,380 B1 | 8/2001 | Van Wesenbeeck et al. |
| 2004/0195531 A1* | 10/2004 | Rahmouni ........... G01N 33/225 250/573 |
| 2017/0269051 A1* | 9/2017 | LaPointe ................ G01N 31/12 |
| 2018/0372013 A1* | 12/2018 | Turlapati ........... F02M 21/0209 |

FOREIGN PATENT DOCUMENTS

| JP | 2004162649 A | 10/2004 |
| JP | 2006047071 A | 2/2006 |
| KR | 1020160086438 | 7/2016 |
| WO | WO2014167219 | 10/2014 |
| WO | WO2016097651 | 6/2016 |
| WO | WO 2016104270 A1 | 6/2016 |

OTHER PUBLICATIONS

International Search Report (English translation of ISR provided) and Written Opinion for PCT/FR2017/053615 dated Apr. 4, 2018.
Andersen, "Algorithm, for Methane Number Determination for Natural Gasses". Project Report. Jun. 3, 1999.
Lötters et al., "Real-Time Composition Determination of Gas Mixtures", IEEE Sensors 2014 Proceedings. Nov. 2, 2014.
Arrhenius et al., "Method Development for Gas Quality Determination in the LNG Storage of a LNG/LCNG Refuelling Station", Sep. 2013. SGC Rapport.
Gieseking et al., "Novel Algorithm for Calculating the Methane Number of Liquefied Natural Gas with Defined Uncertainty", IPC Science and Technology Press. vol. 185. Aug. 20, 2016.
Nippon el al., LNG Fuelled Vessel Technologies Seminar Activities of ClassNK. Jul. 25, 2014.
Office Action dated Sep. 4, 2020 for Japanese Application No. 2019-531898, 7 pages.

* cited by examiner

*Primary Examiner* — Jason K Niesz
(74) *Attorney, Agent, or Firm* — Patterson Thuente Pedersen, P.A.

(57) ABSTRACT

A method for calculating in real time the methane number of a liquefied natural gas contained in a tank, in particular in an on-board tank.

7 Claims, No Drawings

METHOD FOR CALCULATING IN REAL TIME THE METHANE NUMBER MN IN THE LIQUID PHASE OF A LIQUEFIED NATURAL GAS

RELATED APPLICATIONS

This present application is a National Phase entry of PCT Application No. PCT/FR2017/053615 filed Dec. 15, 2017, which claims priority to French Application No. 1662507 filed Dec. 15, 2016, the contents of each being incorporated herein by reference in their entireties.

TECHNICAL FIELD

The present invention generally relates to a method for calculating in real time the methane number of a liquefied natural gas contained in a tank, and in particular in an on-board tank.

BACKGROUND ART

The fuel LNG is a simple and effective alternative to conventional fuels, all from the standpoint of $CO_2$ emission, polluting particles, and energy density. More and more actors are turning towards the use thereof, like road, sea and rail transporters.

However, contrary to conventional refined fuels, LNG does not have a standard composition. According to the placement of the deposit, LNG can contain, in addition, at least heavy compounds (C2, C3, C4, etc.).

The variance of the composition implies a difficulty: the phenomenon of knocking can be declared in engines when the share of heavy compounds is high; it is due to an incorrect combustion triggered by heavy hydrocarbons at an incorrect time at the incorrect place, leading to a second combustion front: hence the arrival of performance, efficiency and mechanical strength problems, even the engine stopping, etc. The methane number is the parameter making it possible to provide the appearance of this phenomenon and to trigger the necessary corrective actions.

To resolve this problem of the knocking phenomenon appearing, the methane number must be as stable as possible. Yet, the methane number is today a magnitude that is hardly known, and of which the determination methods are very diverse as regards the result. The method currently used consisting of calculating a methane number from an LNG composition received at the terminal remains therefore a theoretical view, in addition knowing that this number varies with ageing, according to the method for bunkering the tank used and according to the calculation rule selected. The capacity for determining the methane number is therefore an essential challenge to democratise and encourage the retail LNG fuel market to develop.

In the current state of the art, only detecting a first knocking makes it possible to detect a derivative of the methane number making it possible to then carry out the necessary corrections: the technique currently used is detecting knocking by sound sensor, which triggers a modification of the engine system to adapt the air inlet and to prevent subsequent knocking.

To determine the methane number of an LNG, solutions based on determining the composition of the gaseous phase are known to a person skilled in the art, which make it possible to approach the methane number. This determination of the gaseous phase can, in particular, be carried out as follows:

by optical measurement by spectrometry: this makes it possible for a sufficient precision on heavy hydrocarbons, but not on nitrogen which is used to cut off the gas in view of controlling the methane number (the spectrometry measures the spectral response of only CH bonds). In addition, such a method for determining the composition is only used today for petrol engines (there is therefore also an uncertainty on the capacity thereof to meet the need of LNG). Finally, such a method is very expensive, as the cost of the optical sensor is around 100 USD;

by calculation by empirical correlation with temperature and pressure sensors: the cost of such a solution represented, currently, more than a third of the cost of an LNG tank, which is quite dissuasive. Furthermore, temperature and pressure sensors currently known are typically intended for petrol engines and should, if necessary, also be adapted to LNG;

by measurement by chromatography: the volume and the cost of the equipment make this solution inconsiderable with an on-board tank.

SUMMARY

In order to overcome the disadvantages above, the applicant has implemented a method for calculating in real time the methane number MN of a liquefied natural gas (generally designated by the acronym, LNG) contained in a tank such as an on-board tank. This method for calculating the methane number is based on determining the composition of an LNG in multicomponent liquid phase, which only advantageously uses three types of different sensors. This determination is thus economical and does not involve any gaseous phase measurements.

The solutions known from the prior art (cited above) seek to approach the value of the methane number from determining the composition of the gaseous phase; they therefore find values which do not correspond to the real quality of the gas injected into the engine. Indeed, the composition of the gaseous phase is different from that of the liquid phase, due to the differences in volatility of the components.

Yet, current injection technologies favor the vaporization of liquid LNG. It is therefore this composition of the liquid phase which must be approached. Once the composition is known, it becomes simple to approach the methane number by a calculation, depending on the standard selected.

More specifically, embodiments of the present invention therefore relate to a method for calculating in real time the methane number MN of a liquefied natural gas contained in a tank containing natural gas being distributed into:

a layer of natural gas (11) in the liquid state (1) defined at a given instant t by the temperature T(t) thereof and the density p(t) thereof, said layer of natural gas (11) being in balance with a layer of natural gas (12) in the gaseous state (g), the method being characterized in that it consists of an algorithm comprising, at a given instant t, the following steps:

A. determining, by measuring, the temperature $T_0(t)$ and the density $p_0(t)$ of the layer of natural gas in the liquid state, as well as the pressure Po(t) of the layer of natural gas in the gaseous state (g);

B. approached calculation of the composition of liquefied natural gas contained in the tank, by a stressed minimum calculation algorithm, the algorithm comprising the following sub-steps:

b1) determining, by calculating stressed minimum, a first composition of density $p_0(t)$ and to pressure Po(t), or a first envelope of compositions having the same density $p_0(t)$ to pressure Po(t);

b2) determining, by calculating stressed minimum, a second envelope of compositions having the same density $p_0(t)$ to temperature $T_0(t)$ and to pressure Po(t), and of which the temperature balance $T_{eq}(t)$ to pressure Po(t) is equal to $T_0(t)$;

b3) determining a non-singular point of the second envelope giving a composition approaching the real composition of LNG; and b4) calculating the methane number MN from the approaching composition.

The calculation method according to the invention is implemented by computer.

By tank, this means, in the sense of embodiments of the present invention, a pressurized tank or tank at ambient pressure, of the methane or gas terminal type.

By temperature balance $T_{eq}$ (or bubble temperature), this means, in the sense of embodiments of the present invention, the temperature from which the first bubbles appear when it is heated, at the pressure of the expansion space.

In the scope of the method according to embodiments of the invention, and in particular, of step A, measuring the temperature $T_0(t)$ is carried out using at least one temperature sensor. However, in order to ensure the homogeneity of the measurement in the LNG tank, it is possible to advantageously use several temperature sensors, for example, a sensor in the expansion space and three sensors in the layer of natural gas in the liquid state, as illustrated in FIG. 1 (see example 1).

In the scope of step A of the method according to an embodiment of the invention, measuring the density $p_0(t)$ of the layer of natural gas in the liquid state is carried out using at least one density sensor. One single sensor can be sufficient for measuring the density, the LNG being relatively homogenous in terms of composition and temperature in a storage tank.

In the scope of step A of the method according to an embodiment of the invention, measuring the pressure Po(t) of the layer of natural gas in the gaseous state (g) is carried out using at least one pressure sensor. One single sensor can be sufficient for measuring the pressure, the pressure being homogenous in the gaseous phase.

The method according to an embodiment of the invention has the advantage of being able to approach the composition of an LNG, with a very low margin of error (less than 5%), from measurements taken by three types of different sensors (in particular, temperature and density of the liquid phase of the natural gas, and the pressure of the gaseous phase thereof).

Indeed, if the theory is shared, that LNG, of which is sought to determine the composition, and subsequently the MN number, contains up to compounds of C5 and of nitrogen, conventionally 9 elements can be listed that comprise it, namely: $CH_4$, $C_2H_6$, $C_3H_8$, $iC_4H_{10}$, $nC_4H_{10}$, $iC_5H_{12}$, $nC_5H_{12}$, $C_6H_{14}$ and $N_2$. By assuming that a physical magnitude provides an equation connecting the molar fractions of each component, it would be necessary to obtain 8 different items of information (the fraction of the last component being deducted from the 8 others).

To this end, the method according to an embodiment of the invention shares three key measurable parameters, which are temperature, density of the liquid phase of LNG and the pressure of the gas, to which it adds ideal "statistical" conditional theories (such as encountered in the LNG industry and defined in publications by the GIIGNL (International Group of Liquefied Natural Gas Importers[1]), and uses a non-linear optimization algorithm implemented by a calculator (for example, a microprocessor or a PC) in order to resolve the equation (connecting the molar fractions of each component) in view of obtaining the methane number.

The main step of the method according to an embodiment of the invention is step B of the approached calculation of the composition of the liquefied natural gas contained in the tank by a stressed minimum calculation algorithm implemented by a calculator. As soon as a user wishes to know the characteristics of an LNG (composition, MN number), the calculator executes the algorithm in order to determine the composition of the LNG from the temperature, the pressure and the density.

This calculation is based on a main theory: the LNG is balanced with the gaseous phase thereof, i.e. that the liquid is located thermodynamically on the bubble curve thereof. This assumption is the cornerstone of the calculation. Indeed, assuming the balanced LNG (which is the case most of the time in an LNG storage) makes it possible to put through the temperature, the pressure and the composition of the LNG. This equation and the value of the density (depending on the composition) thus form a system to resolve, in order to determine the composition.

The algorithm of the method according to an embodiment of the invention makes it possible to give, in three steps (steps b1 to b3), a set of possible compositions of the LNG:

first, an LNG composition or an envelope of LNG compositions having the density $p_0(t)$ measured at the measured pressure Po(t) is determined (step b1); then from the composition or envelope of compositions calculated in step b1, a second envelope of compositions are determined, of which the temperature balance $T_{eq}(t)$ to pressure Po(t) is equal to the temperature measured $T_0(t)$ (step b2);

thus a non-singular point is determined, giving a composition approaching the real composition of the LNG (step b3).

In order to reduce the space of the solutions (i.e. the possible compositions) obtained from each of the steps b1 and b2, these are the stressed minimum calculation steps of gradient type (conjugate gradient, projected Newton, interior point, etc.).

The methane number MN is then calculated (step b4) from the approaching composition obtained in step b3. This calculation is simple and uses one of the standard calculations of the LNG industry (AVL method of the titled company, CARB method proposed by SAE International, GRI method of the Gas Research Institute, etc.).

Whatever the calculation method used, the methane number is a dimensionless number of between 0 and 100, the value "0" corresponding in theory to a composition comprising 100% hydrogen and the value "100" corresponding to a composition comprising 100% methane.

For a calculation error on the composition approaching around 5 to 10%, it is possible to achieve a precision on the value of the methane number less than 0.2% according to the physical temperature and pressure conditions.

According to a first advantageous embodiment of step b1) of the method according to the invention, determining the first envelope of compositions can be carried out as follows, by seeking to resolve the following equations:

$$\min \rho(x, P\circ) - \rho_0$$

$$\text{s.t.} \begin{cases} \rho(x, P\circ) - \rho_0 \geq 0 \\ \sum x_i = 1 \\ x_i^l \leq x_i \leq x_i^u \end{cases}$$

with:

p meaning the density calculated from x and Po, $p_0$ meaning the density measured, Po meaning the pressure measured, x meaning the composition vector, composed of $x_i$, $x_i$ meaning the molar fraction of the component i, the exponents l and u respectively making reference to the lower and upper limit of this molar fraction.

According to a second advantageous embodiment of step b1) of the method according to an embodiment of the invention, determining the first envelope of compositions can also be carried out as follows, by seeking to resolve the following equations:

$$\min((\rho(x, P\circ) - \rho_0)^2)$$

$$\text{s.t.} \begin{cases} \sum x_i = 1 \\ x_i^l \leq x_i \leq x_i^u \end{cases}$$

with:

p meaning the density calculated from x and Po, $p_0$ meaning the density measured, Po meaning the pressure measured, x meaning the composition vector, composed of $x_i$, $x_i$ meaning the molar fraction of the component i, the exponents l and u respectively making reference to the lower and upper limit of this molar fraction. It is clear for a person skilled in the art to find other embodiments of step b1) from two advantageous embodiments described above, by using other known types of stressed minimum calculation.

According to a first advantageous embodiment of step b2) of the method according to the invention, determining the second envelope of compositions can be carried out as follows by seeking to resolve the following equations:

$$\min T_{eq}(x, P\circ) - T_0$$

$$\text{s.t.} \begin{cases} T_{eq}(x, P\circ) - T_0 \geq 0 \\ \rho(x, P\circ) - \rho_0 = 0 \\ \sum x_i = 1 \\ x_i^l \leq x_i \leq x_i^u \end{cases}$$

with:

$T_0$ meaning the temperature measured, $T_{eq}$ meaning the temperature balance of LNG at pressure Po, p, $p_0$, x, $x_i$ and u being such as defined above.

According to a second advantageous embodiment of step b2) of the method according to the invention, determining the second envelope of compositions can be carried out as follows by seeking to resolve the following equations:

$$\min((T_{eq}(x, P\circ) - T_0)^2)$$

$$\text{s.t.} \begin{cases} \rho(x, P\circ) - \rho_0 = 0 \\ \sum x_i = 1 \\ x_i^l \leq x_i \leq x_i^u \end{cases}$$

with:

$T_0$ meaning the temperature measured, $T_{eq}$ meaning the temperature balance of LNG at pressure Po, p, $p_0$, x, $x_i$ and u being such as defined above.

It is clear for a person skilled in the art to find other embodiments of step b2) from two advantageous embodiments described above, by using other known types of stressed minimum calculation.

According to a first advantageous embodiment of step b3) of the method according to the invention, the non-singular point of the second envelope can be the barycenter of the second envelope or the point of the second envelope which is the closest to the barycenter of the second envelope.

According to a second advantageous embodiment of step b3) of the method according to the invention, the non-singular point of the second envelope can be calculated as the re-standardized average of the standardized compositions of the second envelope.

Other embodiments of step b3) are possible from the two advantageous embodiments described above, by using other known types of singular points.

Other advantages and particularities of the present invention will result from the following description, given as a non-limiting example and made in reference to the single appended figure, schematically representing a tank example containing natural gas with different temperature, density and pressure sensors.

DETAILED DESCRIPTION

More specifically, FIG. 1 shows a horizontal tank 1 containing natural gas being distributed into:

a layer of natural gas 11 in the liquid state 1 defined at a given instant t by the temperature T(t) thereof and the density p(t) thereof, this layer of natural gas 11 being in balance with a layer of natural gas 12 in the gaseous state g, defined at a given instant t by the pressure P(t).

The tank 1 comprises:

a plurality of temperature sensors 21, 22, 23, 24 to determine the temperature $T_0(t)$ of the LNG, these sensors are arranged on a support 25, one of them 21 being located in the gaseous phase (or expansion space) of the LNG, and three of them being located in the liquid phase (the temperature of the gas is not considered in the calculation), a density sensor 26 to determine the density $p_0(t)$ of LNG in the liquid state (one single sensor is sufficient as the LNG in the liquid state has a homogenous density), and a pressure sensor 31 to determine the pressure Po(t) of the expansion space.

Once measured at each instant, the temperature values $T_0(t)$, of density $p_0(t)$ and the pressure Po(t), these are injected in a calculator implementing the method according to the invention to define a composition approaching LNG. The results of these simulations are presented in example 1 below.

The calculation method according to the invention illustrated in more detail in the example below.

EXAMPLE

The example below is made with a limited number of points (envelope of 6 compositions) for educational purposes in order to facilitate the reading thereof and the understanding of the argument by a person skilled in the art. They can easily understand, by simply deducting that by increasing the number of measuring points, a result of the number is arrived at, of which the precision will increase with the number of measuring points.

The inlet parameters of the method according to the invention are as follows:

$T_0(t) = -160.76°$ C.;
$p_0(t) = 448.11$ g/cm$^3$;
$Po(t) = 1190$ mbar.

From these values, an LNG composition is thus determined, having the density $p_0(t)$ measured at the pressure measured $Po(t)$ (step b1). This first composition is given in Table 1 below.

TABLE 1 first composition

| LNG components | % mol (first composition) |
|---|---|
| CH$_4$ | 91.09 |
| C$_2$H$_6$ | 7.14 |
| C$_3$H$_8$ | 1.54 |
| iC$_4$ | 0.117 |
| nC$_4$ | 0.01 |
| iC$_5$ | 0 |
| nC$_5$ | 0 |
| C$_6$ | 0 |
| N$_2$ | 0 |

For this first composition, the temperature balance has been calculated by a conventional phase envelope calculation method (for example, the Rachford-Rice method)[2], which is $-158.36°$ C. The density $p(t)$ is recalculated for verification: $p(t) = 448.11$ g/cm$^3$ for $T_0(t) = -160.76°$ C.

Then, from this first composition calculated in step b1, an envelope of compositions is determined, of which the temperature balance $T_{eq}(t)$ at pressure $Po(t)$ is equal to the temperature measured $T_0(t)$, that is $-160.76°$ C. (step b2). This envelope comprises six compositions C1 to C6, which are detailed in Table 2 below:

TABLE 2 envelope of compositions for which $T_{eq}(t) = T_0(t)$

| LNG composition | % mol (C1) | % mol (C2) | % mol (C3) | % mol (C4) | % mol (C5) | % mol (C6) |
|---|---|---|---|---|---|---|
| CH$_4$ | 91.89 | 90.07 | 92.56 | 91.8 | 92.57 | 92.14 |
| C$_2$H$_6$ | 5.97 | 8.52 | 5 | 6.16 | 5 | 5.7 |
| C$_3$H$_8$ | 1.45 | 0.267 | 1.22 | 1.35 | 1.22 | 1.15 |
| iC$_4$ | 0 | 0 | 0.27 | 0.002 | 0.27 | 1.15 |
| nC$_4$ | 0 | 0 | 0.27 | 0.002 | 0.27 | 0 |
| iC$_5$ | 0 | 0 | 0 | 0 | 0 | 0 |
| nC$_5$ | 0 | 0 | 0 | 0 | 0 | 0 |
| C$_6$ | 0 | 0 | 0 | 0 | 0 | 0 |
| N$_2$ | 0.679 | 0.721 | 0.654 | 0.682 | 0.654 | 0.67 |

For this envelope of compositions C1 to C6, the temperature balance has been calculated (also by a conventional phase envelope calculation method such as the Rachford-Rice method)[2]: $T_{eq}(t) = -160.76°$ C., that is the temperature $T_0$ measured, which shows that the calculation is carried out correctly.

From this envelope of compositions C1 to C6, a non-singular point is determined from the second envelope giving a composition approaching the real composition of LNG. The methane number MN is then calculated (step b4) from the approaching composition obtained in step b3.

In a first case, the barycenter giving a composition approaching the real composition of LNG as taken as a non-singular point (step b3), given in table 3 below:

TABLE 3 composition of the barycenter

| LNG components | % mol |
|---|---|
| CH$_4$ | 91.8383333 |
| C$_2$H$_6$ | 6.05833333 |
| C$_3$H$_8$ | 1.1095 |
| iC$_4$ | 0.282 |
| nC$_4$ | 0.09033333 |
| iC$_5$ | 0 |
| nC$_5$ | 0 |
| C$_6$ | 0 |
| N$_2$ | 0.67666667 |

The methane number MN is then calculated (step b4) from the approaching composition obtained in step b3. This calculation is simple and uses standard calculation methods of the LNG industry (CARB, GRI H/C, linear coefficient GRI, and MON/KIWA, MWM, AVL), which are empirical methods well-known to a person skilled in the art based on different experiences and engine types. The MWM and AVL methods are the most commonly used public methods in the industry.

The results of these calculations are indicated in Table 4 below for each of the different methods for calculating the methane number, from the composition of Table 3.

TABLE 4 methane number MN

| MN (CARB method) | 86.9427269 |
|---|---|
| MN (GRI H/C method) | 79.9123525 |
| MN (linear coefficient GRI method) | 81.1445809 |
| MON/KIWA method | 78.9080193 |
| MWM method | 78 |
| AVL method | 78.7 |

It is noted, that the different methods give different results. This is normal as there is no agreement today in the industry on the method to be used to calculate the methane number. Different methods exist, and each company has a predilection method. Other calculation methods, less expansive, exist and can all also be used from the composition determined above.

In a second case, from the envelope of compositions C1 to C6 obtained above, the re-standardized average of the standardized compositions of the second envelope is taken as a non-singular point, of which the composition is given in Table 5 below:

TABLE 5 second composition

| LNG components | % mol |
|---|---|
| CH$_4$ | 91.7873393 |
| C$_2$H$_6$ | 6.05721857 |
| C$_3$H$_8$ | 1.10826957 |

TABLE 5-continued

| second composition | |
| --- | --- |
| LNG components | % mol |
| $iC_4$ | 0.28047889 |
| $nC_4$ | 0.09035225 |
| $iC_5$ | 0 |
| $nC_5$ | 0 |
| $C_6$ | 0 |
| $N_2$ | 0.67634147 |

The methane number MN is then calculated (step b4) from this approaching composition obtained in step b3 (given in Table 5) by using the standard calculation methods of the LNG industry described above (MWM, AVL). The results of the methane number calculations are indicated in Table 6 below for each of the different methods used, from the composition of Table 5.

TABLE 6

| methane number MN | |
| --- | --- |
| MN (CARB method) | 86.9479438 |
| MN (GRI H/C method) | 79.9169944 |
| MN (linear coefficient GRI method) | 81.0463815 |
| MON/KIWA method | 78.9166216 |
| MWM method | 77 |
| AVL method | 78.7 |

It is observed that the values calculated in Table 6 are close to those of Table 4.

All the differences between Table 4 and Table 6 are less than 0.2%, except for that for the MWM method, of 1.3%. The MWM method is known in the industry to not be a stable method and give difference of absolute 1 for very close compositions, therefore this result could be expected.

LIST OF REFERENCES

[1] http://www.giignl.org/publications
[2] *Procedure for use of electronic digital computers in calculating flash vaporization hydrocarbon equilibrium.* RACHFORD Jr, H. H., & RICE, J. D. s.l.: Journal of Petroleum Technology, 1952, Vol. 4(10), 19-3.

The invention claimed is:

1. Method providing the actual value of the methane number MN of a liquefied natural gas for triggering corrective action to the incorrect combustion of hydrocarbons in an engine, or to a system that regulates the engine functioning, of a transporter, the transporter including a transporter tank, the method implemented by computer to calculate in real time the methane number MN of the liquefied natural gas contained in the transporter tank, the transporter tank containing natural gas for use in combustion, the transporter tank including a tank liquid holding space for holding the natural gas in a liquid phase and an expansion space for containing the natural gas in a gaseous phase, the natural gas being distributed into:
 a layer of natural gas in the liquid state defined at a given instant t by the temperature T(t) thereof and the density p(t) thereof, said layer of natural gas in the liquid state held in the tank liquid holding space and being in balance with
 a layer of natural gas in the gaseous state (g) contained in the tank expansion space, the layer of natural gas in the gaseous state defined at a given instant t by the pressure P(t) thereof;

said method, at a given instant t, including the following steps of:
 A. positioning at least one temperature sensor in the tank expansion space, positioning a plurality of additional temperature sensors in the tank liquid holding space, positioning a density sensor in the tank liquid holding space, and positioning a pressure sensor in the tank expansion space;
 B. determining, by measuring, the temperature To(t) and the density po(t) of the layer of natural gas in the liquid state with the plurality of additional temperature sensors and the density sensor in the tank liquid holding space, and the pressure Po(t) of the layer of natural gas in the gaseous state (g) with the pressure sensor in the tank expansion space;
 C. approaching the calculation of the composition of liquefied natural gas contained in the tank, by a stressed minimum calculation algorithm, said algorithm comprising the following sub-steps:
  c1) determining, by calculating stressed minimum, a first composition of density po(t) and to pressure Po(t), or a first envelope of compositions having the same density po(t) to pressure Po(t);
  c2) determining, by calculating stressed minimum, a second envelope of compositions having the same density po(t) to temperature $T_0(t)$ and to pressure Po(t), and of which the temperature balance $T_{eq}(t)$ to pressure Po(t) is equal to $T_0(t)$;
  c3) determining a non-singular point of the second envelope giving a composition approaching the real composition of LNG; and
  c4) calculating the methane number MN from said approaching composition; and providing the engine, or the system that regulates the engine functioning, the correct value of the methane number MN of the natural gas entering the engine, so that the engine, or the system that regulates the engine functioning, triggers the corrective action regarding the engine functioning in general, especially the combustion of the natural gas; and, and triggering the corrective action when the calculated methane number MN indicates the incorrect combustion of hydrocarbons.

2. Method according to claim 1, wherein step c1) for determining the first envelope of compositions is carried out as follows, by seeking to resolve the following equations:

$$\min \rho(x, P\circ) - \rho_0$$
$$s.t. \begin{cases} \rho(x, P\circ) - \rho_0 \geq 0 \\ \sum x_i = 1 \\ x_i^l \leq x_i \leq x_i^u \end{cases}$$

with:
 p meaning the density calculated from x and Po,
 p0 meaning the density measured,
 Po meaning the pressure measured,
 x meaning the composition vector, composed of $x_i$,
 $x_i$ meaning the molar fraction of the component i, the exponents 1 and u respectively making reference to the lower and upper limit of this molar fraction.

3. Method according to claim 1, wherein step c1) for determining the first envelope of compositions is carried out as follows, by seeking to resolve the following equations:

$$\min((\rho(x, P\circ) - \rho_0)^2)$$

$$\text{s.t.} \begin{cases} \sum x_i = 1 \\ x_i^l \leq x_i \leq x_i^u \end{cases}$$

with:

p meaning the density calculated from x and Po, p0 meaning the density measured, Po meaning the pressure measured, x meaning the composition vector, composed of xi, $x_i$ meaning the molar fraction of the component i, the exponents 1 and u respectively making reference to the lower and upper limit of this molar fraction.

4. Method according to claim 1, wherein step c2) for determining the second envelope of compositions is carried out as follows by seeking to resolve the following equations:

$$\min T_{eq}(x, P\circ) - T_0$$

$$\text{s.t.} \begin{cases} T_{eq}(x, P\circ) - T_0 \geq 0 \\ \rho(x, P\circ) - \rho_0 = 0 \\ \sum x_i = 1 \\ x_i^l \leq x_i \leq x_i^u \end{cases}$$

with:

$T_0$ meaning the temperature measured, $T_{eq}$ meaning the temperature balance of LNG at pressure Po, p meaning the density calculated from x and Po, p0 meaning the density measured, Po meaning the pressure measured, x meaning the composition vector, comprised of $x_i$, $x_i$ meaning the molar fraction of the component i, the exponents 1 and u respectively making reference to the lower and upper limit of this molar fraction.

5. Method according to claim 1, wherein step c2) for determining of the second envelope of compositions and carried out as follows by seeking to resolve the following equations:

$$\min((T_{eq}(x, P\circ) - T_0)^2)$$

$$\text{s.t.} \begin{cases} \rho(x, P\circ) - \rho_0 = 0 \\ \sum x_i = 1 \\ x_i^l \leq x_i \leq x_i^u \end{cases}$$

with:

$T_0$ meaning the temperature measured, $T_{eq}$ meaning the temperature balance of LNG at pressure $P_0$, p meaning the density calculated from x and Po, p0 meaning the density measured, Po meaning the pressure measured, x meaning the composition vector, comprised of $x_i$, $x_i$ meaning the molar fraction of the component i, the exponents 1 and u respectively making reference to the lower and upper limit of this molar fraction.

6. Method according to any one of the claim 1, wherein the non-singular point of the second envelope is the barycenter of the second envelope or the point of the second envelope which is the closest to the barycenter of the second envelope.

7. Method according to claim 1, wherein the non-singular point of the second envelope is calculated as the re-standardized average of the standardized compositions of the second envelope.

* * * * *